(12) United States Patent
Hagg et al.

(10) Patent No.: US 9,044,545 B2
(45) Date of Patent: Jun. 2, 2015

(54) NEEDLELESS INJECTION DEVICE

(71) Applicant: ERBE Elektromedizin GmbH, Tuebingen (DE)

(72) Inventors: Martin Hagg, Wannweil (DE); Ralf Kühner, Stuttgart (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 0 days.

(21) Appl. No.: 14/079,114

(22) Filed: Nov. 13, 2013

(65) Prior Publication Data

US 2014/0142536 A1    May 22, 2014

(30) Foreign Application Priority Data

Nov. 16, 2012    (EP) ..................................... 12192953

(51) Int. Cl.
  *A61M 5/30*    (2006.01)
  *A61B 17/00*    (2006.01)
  *A61B 17/3203*    (2006.01)
  *A61B 17/32*    (2006.01)

(52) U.S. Cl.
  CPC ............ *A61M 5/30* (2013.01); *A61B 17/00234* (2013.01); *A61B 2017/00269* (2013.01); *A61B 17/32037* (2013.01); *A61B 17/3203* (2013.01); *A61B 2017/00544* (2013.01); *A61B 2017/00548* (2013.01); *A61B 2017/320044* (2013.01)

(58) Field of Classification Search
  CPC ... A61M 5/30; A61M 5/2046; A61M 5/2053; A61M 5/3015; A61M 5/3007
  USPC ..................... 604/68–72, 131, 140–141, 143, 604/145–148
  See application file for complete search history.

(56) References Cited

U.S. PATENT DOCUMENTS 4,342,310 A * 8/1982 Lindmayer et al. ............. 604/70
5,553,741 A * 9/1996 Sancoff et al. ..................... 222/1
5,700,245 A * 12/1997 Sancoff et al. ................ 604/145

(Continued)

FOREIGN PATENT DOCUMENTS

DE        69533811 T2    12/2005
JP        2001-224684 A    8/2001
JP        2001-16689 A    6/2005

OTHER PUBLICATIONS

European Search Report, related Application No. EP 12192953.3 dated Apr. 18, 2013, 6 pages.

(Continued)

*Primary Examiner* — Quynh-Nhu H Vu
(74) *Attorney, Agent, or Firm* — Fitch, Even, Tabin & Flannery LLP

(57) ABSTRACT

A fluid applicator is fed by a fluid delivery arrangement containing an energy storage such as a pressure vessel. The gas pressure acts on a container that has been prefilled with the ejection fluid. The fluid to be ejected is thus subject to constant pressure. With a valve, the user can initiate the ejection of the desired amount of fluid with constant intensity. The check valve may also be a regulating valve which can be used by the user to vary the intensity of the effect. The user need only release the system, e.g., by puncturing the pressure vessel, to then be able to directly inject the fluid in a defined or metered manner via the probe, i.e., the fluid applicator. It is also possible to configure the entire injection device as a single-use system and to prefill the fluid applicator up to its fluid exit opening.

9 Claims, 2 Drawing Sheets

(56) References Cited

U.S. PATENT DOCUMENTS

| | | | |
|---|---|---|---|
| 5,891,086 A * | 4/1999 | Weston | 604/70 |
| 5,957,897 A | 9/1999 | Jeffrey | |
| 6,096,002 A * | 8/2000 | Landau | 604/68 |
| 7,686,788 B2 * | 3/2010 | Freyman et al. | 604/181 |
| 2001/0031945 A1 | 10/2001 | Haar et al. | |
| 2002/0143323 A1 | 10/2002 | Johnston et al. | |
| 2005/0038406 A1 * | 2/2005 | Epstein et al. | 604/500 |
| 2005/0209562 A1 | 9/2005 | Kim | |
| 2006/0149193 A1 | 7/2006 | Hall | |
| 2009/0157114 A1 | 6/2009 | Fischer et al. | |
| 2012/0065615 A1 * | 3/2012 | Boyd et al. | 604/500 |

OTHER PUBLICATIONS

Japanese office action in corresponding Japanese Application No. JP2013-236400, dated Feb. 17, 2015, 7 pages.

* cited by examiner

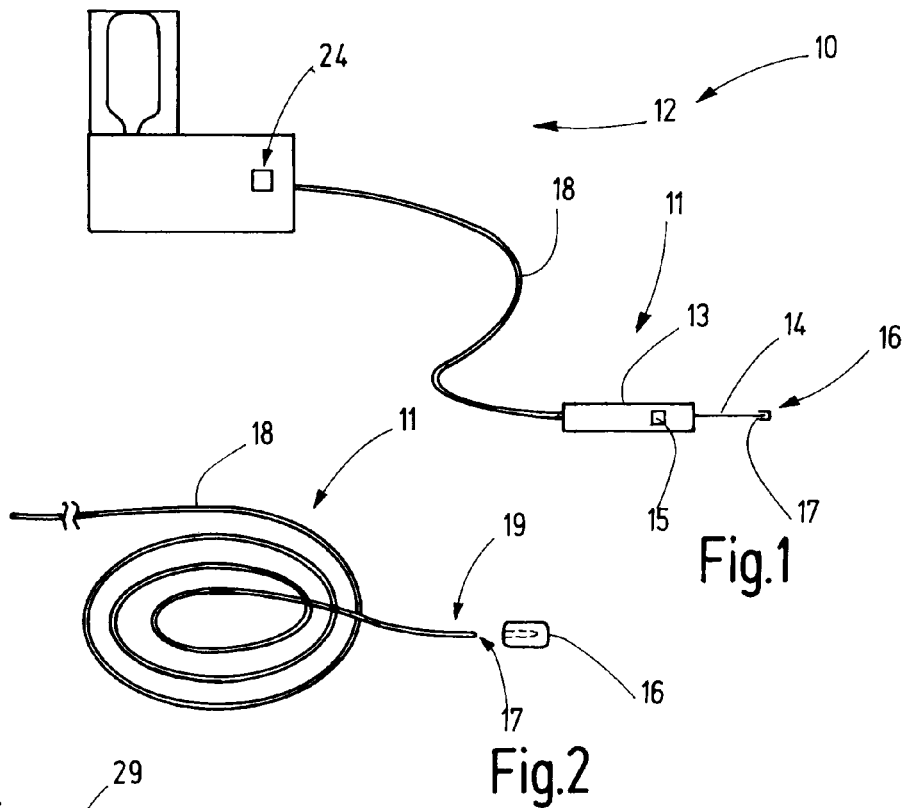
Fig.1
Fig.2
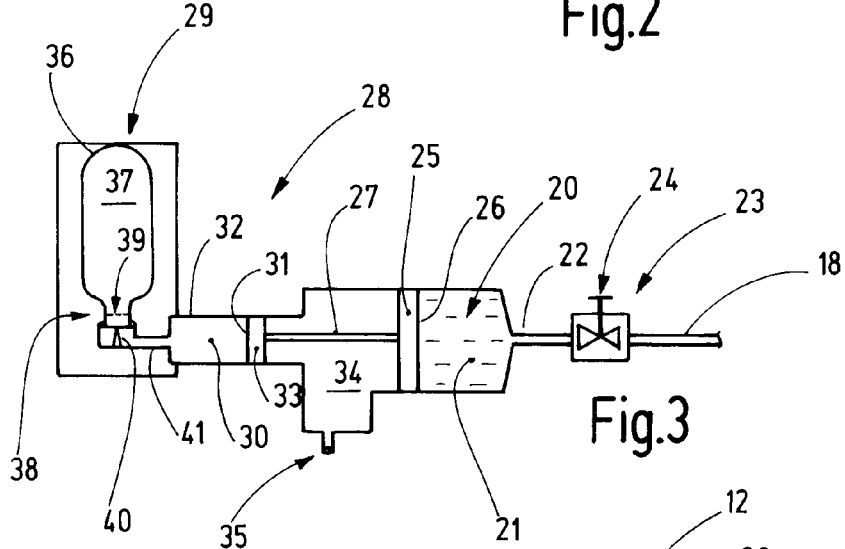
Fig.3
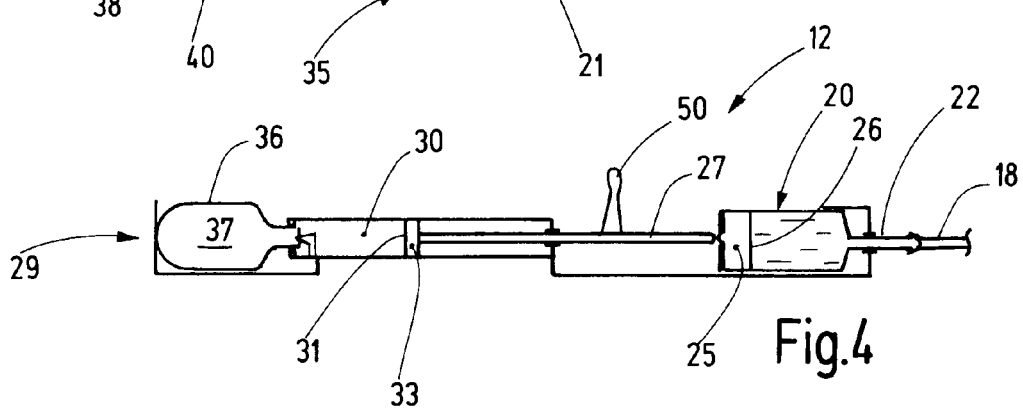
Fig.4

NEEDLELESS INJECTION DEVICE

RELATED APPLICATION(S)

This application claims the benefit of European Patent Application No. 12192953.3 filed Nov. 16, 2012, the contents of which are incorporated herein by reference as if fully rewritten herein.

TECHNICAL FIELD

The invention relates to an injection device for the needleless fluid injection, in particular an injection for lifting or for elevating the mucosa of the gastrointestinal tract or for similar applications.

BACKGROUND

Automatic injection devices have been known for the administration of medications, said devices operating with the use of a spring storage and a needle. Publication DE 69533811 T 2 discloses such an example. The device comprises a medication storage vessel that is connected to a hollow needle. In inoperative position, this needle is retracted into a housing. A tensioned spring in the housing is disposed to allow the hollow needle to spring forward when triggered and to eject the medication through the hollow needle.

Furthermore, devices used for the needleless submucosal injection of a fluid have been known. For example, publication U.S. 2009/0157114 A1 discloses an endoscope comprising a probe for the needleless submucosal injection. To accomplish this, the probe ejects a jet of sodium chloride solution that, due to its small cross-section and its pressure (or pulse) penetrates the tissue. In order to convey the sodium chloride solution and to generate the appropriate pressure it is possible to provide a pump unit or, optionally, a force-increasing lever.

The application of this principle requires a supply device comprising an appropriate pump unit. If a force-increasing lever is used to generate pressure—optionally in conjunction with an appropriate pressure-resistant syringe—the permanent generation of pressure by using manual force, e.g. by an assistant, is awkward.

SUMMARY

It is an object of the invention to provide an injection device that can be easily and comfortably handled and requires minimal technical effort.

This object is achieved with the injection device in accordance with the invention, said device being designed in particular for the needleless injection for lifting or elevating the mucosa of the gastrointestinal tract; however it can also be used to achieve other comparable objects. The injection device is disposed to generate a fluid jet with the use of a fluid applicator, said jet penetrating the biological tissue without the use of a hollow needle in order to generate a fluid reservoir there. Preferably, the fluid applicator is designed as a flexible thin probe that can be inserted though a tube, an endoscope or other suitable means into a body cavity in order to perform there the desired needleless injection. However, in open surgery, the fluid applicator may also be configured as a manual instrument with a handle and a nozzle by means of which the user initiates the ejection of a fluid jet. Regardless of whether the fluid applicator is configured as a flexible probe or as a manual instrument, the nozzle provided for fluid jet ejection can essentially be configured as a cylindrical, sharp jet or also as other jet configurations, e.g., suitable for parenchymal dissolution (conical jet, fan-shaped jet, hollow jet or the like). It is also possible to use the fluid jet generated by the device in accordance with the invention for the dissection of tissue.

The fluid line for delivery to the fluid exit opening communicates with a supply chamber that belongs to a fluid delivery arrangement. Preferably, the fluid is physiological cooking salt solution. The supply chamber comprises at least a first movable wall surface to which a force generated by a drive arrangement can be applied. Preferably, this force is essentially constant, so that the fluid at the fluid exit opening may exit at an essentially constant velocity and under essentially constant pressure.

The drive arrangement comprises an energy storage. It can be used independently of any stationary apparatus, thus providing great flexibility when used on the patient. Also, the energy storage replaces ancillary staff that, otherwise, would have to manually provide the high fluid pressure necessary for needleless injection. Preferably, the fluid is under a pressure of 20 bar to 40 bar; for example, it is essentially subject to a constant pressure of 30 bar.

In principle, it is possible to use various types of storages for different types of energy. For example, the energy storage may comprise a tensioned spring or be made of such a spring that acts on a movable wall of the storage chamber. In doing so, the length of the spring is preferably greater than that of the path to be traveled by the movable wall source at the time of ejection of the fluid. As a result of this, the change of the spring force at the time of expansion is limited by the expansion of said spring force, so that the resultant pressure difference between the full supply chamber and the almost empty supply chamber remains below a permissible tolerance of, for example, a few bars.

It is possible to associated the spring with a releasable lock and to apply pressure to the fluid only when the lock is released. In inoperative position, the lock absorbs the force coming from the tensioned spring. If the lock is released, the spring acts on the movable wall and applies pressure to the fluid, thus establishing the operational readiness of the injection device.

Alternatively, the energy storage may be an electric battery or a rechargeable battery that is connected to an electric motor via a switch, said electric motor being connected to the movable wall surface of the supply chamber—either directly or via a transmission. The battery has a capacity that, preferably, is at least large enough that the energy provided by it for ejecting the entire fluid volume of the supply chamber is sufficient.

In a preferred embodiment the energy storage is configured as a pressure source. The pressure source is understood to be a supply volume with a pressurized compressible fluid. The fluid may be present—fully or in part—in gaseous or liquid state. Preferably, a fluid such as carbon dioxide ($CO_2$), nitrogen oxide (dinitrogen monoxide, or the like) is used as the fluid at room temperature and at storage pressure. During expansion, said fluid evaporates fully or in part. The use of other (non-boiling) fluids (nitrogen, argon or the like) is possible.

The drive arrangement preferably comprises an expansion chamber having a second movable wall surface for expansion of the driving fluid, in which case the expansion chamber is connected or can be connected to the pressure source. As soon as the pressure source is connected to the expansion chamber the injection device is ready for operation. The pressure exerted by the driving fluid to the second movable wall surface generates a force that can be applied to the first movable wall surface of the supply chamber. If at least part of the driving fluid is present in the liquid phase in the pressure source, a constant operating pressure can be maintained in the expansion chamber during expansion, i.e., during the ejection of the fluid. Accordingly, a constant pressure is applied to the fluid.

Preferably, a $CO_2$ cartridge, an $N_2O$ cartridge or another gas-filled cartridge having a gas-tight seal can be used. The cartridge may be associated with a puncturing arrangement for breaking the seal of the cartridge. As soon as the cartridge is placed in an appropriate receptacle and activated by means of the puncturing device, the injection device is ready for operation. Preferably, the first and the second wall surfaces have differently dimensioned areas. In this manner, a pressure adaptation is effected and, for example, using a $CO_2$ cartridge exhibiting up to 60 bar, a constant ejection pressure of, for example 30 bar can be achieved. The surface ratio of the wall surfaces relative to each other is 1:2 in this case. Other wall surface ratios may be provided. Consequently, a pressure increase, as well as a pressure decrease, can thus be achieved.

Preferably, the two surfaces are arranged on plungers located at a distance from each other, in which case a vent opening is provided between them. In this manner, gas leaking out of the expansion chamber at the plunger may escape without entering the supply chamber. Injury to the patient due to break-through gasses are thus precluded.

Preferably, a valve is provided between the nozzle and the supply chamber. This may be a check valve by means of which the fluid flow can be allowed or blocked. In a convenient embodiment, the value may also be configured as a regulating valve. It allows the user to regulate the force of the exiting fluid jet.

Typically, the valve is arranged in the vicinity of the supply chamber. When the injection device is started, the fluid line must be vented. This is achieved by a test activation of the valve until the entire fluid line is filled with fluid. Alternatively, the fluid exit opening may also be provided with a sterility seal and the fluid line may be prefilled with fluid. This serves to further facilitate handling.

Each of the above-described injection devices may be designed as a single-use device, either fully or in part. A housing containing the supply chamber and the drive arrangement may be provided sterile and of a plastic material, wherein the supply chamber may be filled with sodium chloride solution or another fluid. In the case of a spring drive, the tensioned spring may be located in the housing, said spring being held by the locking arrangement. In the case of the electric motor drive, the housing may accommodate a battery, an electric motor and a transmission. In the preferred embodiment that is actuated by the pressure storage, a sterile package may contain the injection device, as well as the pressure storage, e.g., configured as a $CO_2$ cartridge or another cartridge. For actuation, the cartridge is placed in an appropriate receptacle of the injection device and punctured. It is also possible to use non-sterile storage cartridges (e.g., $NO_2$, $CO_2$ the like) that are available as consumer goods.

Additional details of embodiments of the invention are the subject matter of the drawings, the description or the subordinate claims.

BRIEF DESCRIPTION OF THE DRAWINGS

The drawings depict, schematically and in an exemplary manner, different embodiments of the injection device in accordance with the invention. They show in FIG. 1 a schematized general view of an injection device in accordance with the invention;

FIG. 2 a part of an alternative embodiment of an injection device in accordance with the invention;

FIG. 3 a first embodiment of a fluid supply arrangement of an injection device; and FIGS. 4 through 7 modified embodiments of fluid delivery arrangements for injection devices.

DETAILED DESCRIPTION

Figure 5:
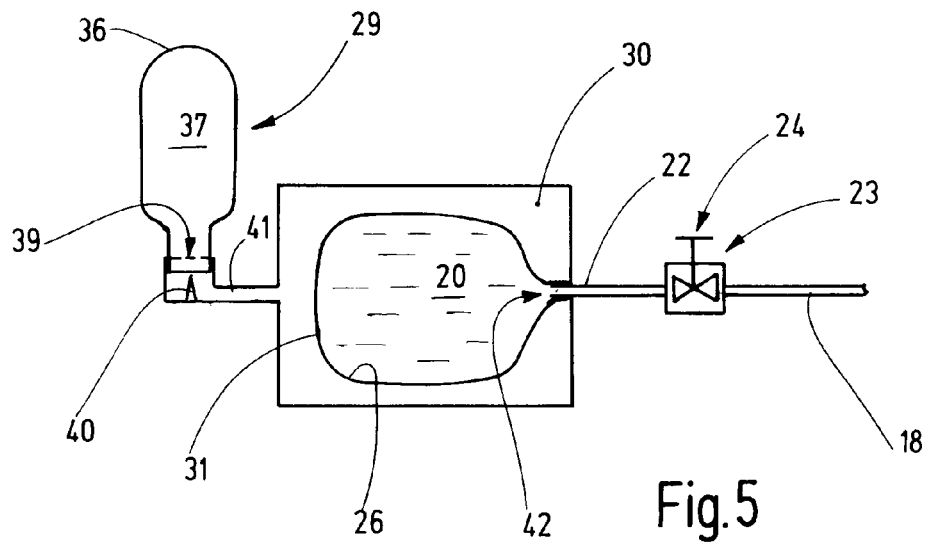

The injection device 10 shown in FIG. 1 comprises a fluid applicator 11 and a fluid delivery arrangement 12 for supplying the fluid applicator 11 with a fluid. Preferably, the fluid is a physiological cooking salt solution (NaCl solution) that is ejected by the fluid applicator 11 in a suitable jet form. Preferably, a sharp, laminar, needle-like jet is preferred. However, it is also possible to provide other situations of application, wherein another jet form is desired and implemented.

As is schematically shown in FIG. 1, the fluid applicator may be provided for open surgical applications and, accordingly, comprise a handle 13 and a nozzle shaft 14 extending from said handle. The handle 13 may have an actuating member, e.g., configured as a button 15, by means of which a valve clearing or blocking the nozzle shaft 14 for the supply, or also a regulating valve, can be actuated. At the distal end of the nozzle shaft 14 there may be provided a fluid exit opening 17 that is closed by a protective cap 16, said opening allowing a fluid jet to exit in the desired form. Preferably, the fluid exit opening 17 is a nozzle. Furthermore, the fluid applicator 11 includes a fluid line 18 that connects the fluid applicator 11 to the fluid delivery arrangement 12. The fluid line 18 conveys the fluid through the handle 13 and, ultimately, to the nozzle shaft 14 and its nozzle.

Whereas FIG. 1 shows a fluid applicator 11 for open surgical applications, FIG. 2 shows a fluid applicator 11 for endoscopic applications. Said applicator essentially comprises the fluid line 18 that is configured here as a thin flexible plastic hose that can be slid through a lumen of an endoscope. It has the fluid exit opening 17 on its distal end 19. If necessary, the exit opening may be defined by a nozzle.

The fluid delivery arrangement 12 is disposed to supply the fluid applicator 11 with a fluid that is essentially under constant pressure. The fluid applicator 11 according to FIG. 1, as well as the fluid applicator 11 according to FIG. 2, can be supplied by any of the hereinafter described fluid delivery arrangements 12.

As shown by FIG. 3, the fluid delivery arrangement 12 comprises a supply chamber 20 that is completely filled with a suitable fluid 21. The supply chamber 20 has an exit 22 to which the fluid line 18 is connected via a valve 23. The valve 23 may be a switching valve that can assume only the two positions of "open" and "closed". Alternatively, this may be a regulating valve that can be used for setting various flow resistances and thus various flow rates. The valve may comprise a control member or an actuating member 24 that is provided on the housing of the fluid delivery arrangement 12.

The supply chamber 20 comprises an accommodation chamber that has the form of a cylinder, for example, that is closed on one side by a movable plunger 25. The cylinder closes the supply chamber 20 with a wall surface 26 that can be moved relative to the remainder of the cylinder in that the plunger 25 can be slid relative to the cylinder in a sealing manner.

Via a force-transmitting means such as, e.g., a pin, a ram, a rod 27 or the like, the plunger 25 is connected to a drive arrangement 28 that contains an energy storage 29. In the present exemplary embodiment, the drive arrangement 28 additionally comprises an expansion chamber 30 that has at least one movable wall surface 31. The ratio of the wall surfaces 26, 31 relative to each other is preferably different from "one". The movable wall surface 31 may be represented by the face of a plunger 33 that is movably supported in a cylinder 32 so as to create a seal. Via the rod 27 or another force-transmitting means, said plunger is connected to the plunger 25. The rod 27 extends through an intermediate space 34 that is fully or partially enclosed by the housing that encloses the supply chamber 20 and the expansion chamber 30. Preferably, the intermediate space 34 is vented toward the atmosphere, for which at least one vent opening 35 is provided.

The energy storage 29 is represented by a pressure source 36, for example, in the form of a $CO_2$ cartridge 37. It represents a pressure-proof container that is provided with a seal 39 on its neck-like end 38. The seal 39 can be punctured by means of a puncturing needle 40 in order to release the gas present in the pressure source or pressure vessel 36, said puncturing needle being part of a vessel receptacle. The vessel receptacle comprises a sealing means in order to accommodate the neck or end 38 of the pressure vessel 36 in a sealing manner. The puncturing needle 40 punctures the seal 39, allowing the thusly released pressurized gas to be conveyed via a channel 41, or also directly (FIG. 4), into the expansion chamber 30.

The injection device 10 described so far operates as follows:

It is assumed that the fluid delivery arrangement 12 is made available with the supply chamber 20 filled. The plungers 25, 33 are thus in the left position in FIG. 3. The valve 23 is closed, and the fluid line 18 is initially empty.

For actuation, the pressure vessel 36 is placed in its receptacle, in which case the seal 39 is punctured. Alternatively, a pre-installed pressure vessel that is already in the receptacle is punctured by means of a suitable mechanism in that said vessel is moved against the puncturing needle 40 or in that the puncturing needle is being moved. The mechanism may be, for example a cam actuated by a manual lever, where the end 38 of the pressure vessel located opposite the neck is supported. Other mechanisms such as toggle arrangements or the like may be provided.

If the pressure vessel 36 is a commercially available $CO_2$ cartridge filled with, e.g., 12 g of $CO_2$, a pressure of 55 bar to 60 bar acts directly on the wall surface 31. The force directed to the right in the related FIG. 3 is transmitted to the plunger 25 via the rod 27. As a result of the cross-sectional ratio of the pistons 33, 25 relative to each other, a desired fluid pressure of, for example, 30 bar can be generated. In this case, the wall surface 26 has twice the area of the wall surface 31.

The user now actuates the valve 23 in order to open it and to fill the fluid line 18 with the fluid up to the fluid exit opening 17. If a protective cap 16 is provided, the user first removes said cap. Now the injection device 10 is ready for use. Depending on the design of the fluid applicator 11, said injection device can be used by the appropriate use of the handle 13 and, optionally, be actuated by actuating the button 15 (if any). If a sharp fluid jet exits from the fluid exit opening 17, said jet can penetrate a biological tissue and be used there for the submucosal injection, for example. Other applications for the injection in and under tissue are possible. For example, the user can also use the exiting jet for dissolving organic tissue. To accomplish this, the fluid exit opening 17 can be designed in such a manner that other forms of jets, e.g., fan-shaped jets or the like, can be produced.

With the use of the fluid applicator 11 as in FIG. 2, said fluid applicator is inserted, e.g., through an endoscope, into a body cavity, e.g., the gastrointestinal tract, in order to perform there, e.g., a submucosal, injection, with the fluid jet exiting from the fluid opening 17.

The fluid supply amount may be from 200 ml to 300 ml. Such a fluid supply can be ejected with the use of a single $CO_2$ cartridge 37 (e.g., 12 g) at an almost constant pressure of 30 bar. Consequently, this results in reliable and constant operating conditions for the user. In doing so, the injection device 10 as such is at all times very easy to handle and can be used independently of an external energy source or of the skill of an assistant.

Modifications are possible. These will be explained in an exemplary manner hereinafter and relate to the fluid delivery arrangement 12, in particular. For example, the pressure vessel 36 may be arranged at an angle relative to the direction of movement of the plunger 33 as shown by FIG. 3, as well as coaxially with respect to said plunger as shown by FIG. 4. As a result of this, a compact, slim design can be achieved. In addition, it is possible both to design the injection device 10 as a whole or only the fluid delivery arrangement 12 as a single-use device or as a multiple-use device. FIG. 4 illustrates this with reference to an example, wherein the supply chamber 20 and its plunger 25 are configured as separately usable assemblies in the manner of a pressure-proof syringe. This syringe is inserted in a receptacle of the housing whereby the rod 27 pushes against the plunger 25. As soon as the pressure vessel 36, e.g., a $CO_2$ cartridge 37, is placed in its respective receptacle, pressure can be applied to the chamber 30, in which case the rod 27 pushes against the plunger 25 with an essentially constant force. Now the procedure may be performed via the fluid line 18 connected to the exit 22 as previously described. The valve 23 may be arranged in the handle 13 or at another location of the fluid line 18.

If the supply chamber 20 is empty, it can be replaced with a sterile full chamber. Likewise, the $CO_2$ cartridge 37 can be discarded, thus initially rendering the expansion chamber 30 without pressure. Via a suitable means 50, it is possible to push the plunger 25 back into its left rest position. In this state, it is possible to insert a new supply chamber 20, i.e., a new syringe and a new $CO_2$ cartridge 37 into the housing, thus rendering the fluid delivery arrangement 12 again ready for operation. In such reusable devices, the expansion chamber 30 may also be connected to a residual pressure removal valve in order to allow existing residual propellant fluid to escape in a hazard-free manner.

As an alternative to the use of cylindrical chambers for the expansion chamber 30 and the supply chamber 20 with appropriate plungers 25, 33, the supply chamber 20 can be arranged in the expansion chamber 30 as in FIG. 5. The supply chamber 20 may be, for example, a pouch or an otherwise compressible vessel that is connected to the exit 22. The inside surface of the pouch represents the first movable wall surface 26. The outside of the pouch represents the second movable wall surface 31. Again, a pressure vessel 36 acts as the energy storage 29 for applying pressure to the expansion chamber 30. As soon as the puncturing needle 40 has punctured the seal 39 provided on the vessel neck of the pressure vessel 36 the expansion chamber 30 is pressurized. This pressure acts on the wall surface 31 and thus, to an equal extent, on the fluid supply in the pouch via the wall surface 26. The pressurized fluid can be released in a specific manner via the valve 23 in order to feed the fluid applicator 11.

The pouch containing the fluid supply may be a single-use product, whereas the housing enclosing the chamber 20 and accommodating the pressure vessel 36 may be disposed for multiple use. Alternatively, it is also possible to design these parts as single-use products.

Preferably, an exit opening 42 terminating on the inside of the supply chamber 20 is provided at the connection 22, said exit opening representing a flow restriction and, for example, having a diameter of only one millimeter or less. The restriction ensures that the flexible wall of the completely emptied pouch closes the corresponding exit opening 42. In doing so, the cross-sectional area of the exit opening 42, is preferably small enough to ensure that the pouch wall in contact with the exit opening will not rupture under the pressure of the $CO_2$ cartridge 37. For example, for this purpose, the diameter of the exit opening 42 is smaller than the wall thickness of the pouch enclosing the supply chamber 20.

Figure 6:
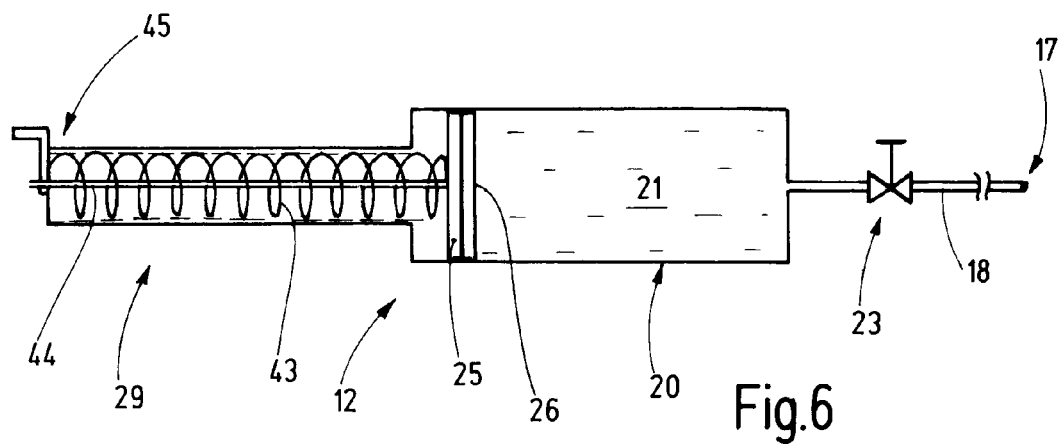

Additional modifications are possible. In view of this, FIG. 6 illustrates a fluid delivery arrangement 12 with an energy storage 29 configured as a spring energy storage. To do so, for example, a previously tensioned compression spring is provided, one end of said spring being supported by the plunger 25 and the other end of said spring being supported by a housing wall. In doing so, the fluid 21 is pressurized via the plunger 25.

It is possible to lock the plunger 25 in the housing—via a pulling means, e.g., a pull rod 44 and a locking arrangement 45. In this case, the pull rod 44 absorbs the force of the compression spring 43. If the locking arrangement 45 is released, for example, by tearing off or removing a blocking pin, the spring force acts on the plunger, thus pressurizing the fluid 21. In doing so, the fluid 21 can be released via the valve 23 and flow out in a controlled manner via the line 18. The fluid delivery arrangement 12 can be designed as a refillable product or as a single-use product.

Figure 7:
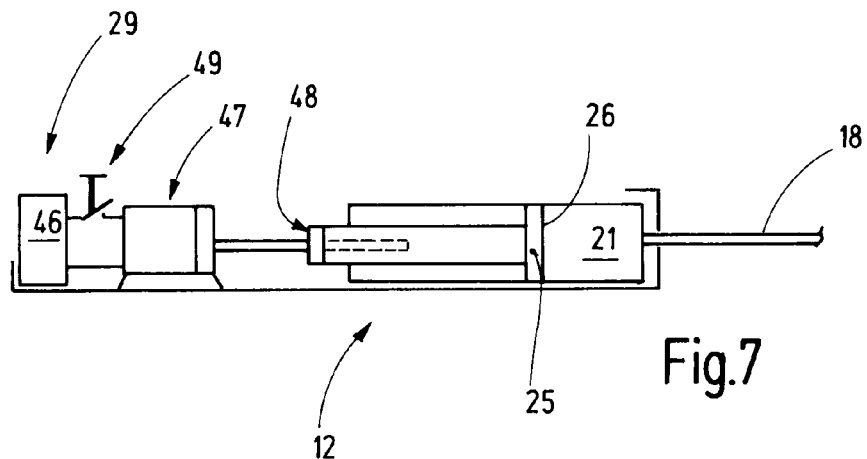

The latter also applies to the embodiment as in FIG. 7. In conjunction with this, the provided energy storage is an electric battery 46 or a rechargeable battery, a supercapacitor, or the like, these being disposed to feed a motor 47. Via a transmission, the motor 47 actuates the plunger 25. Preferably, the transmission is a reduction gear that moves the plunger 25, e.g., via a spindle thread drive 48. A switch 49 is disposed to actuate the motor 47. Preferably, the motor 47 and its feeding arrangement are adapted to each other in such a manner that the motor 47 can be energized over an extended period of time (several minutes). Preferably, in doing so, the motor 47 is designed as a torque motor, so that it can be operated at a rate of revolutions of zero as the torque source. In doing so, it generates an essentially constant torque, independent of its rate of revolutions, said torque producing a constant force acting on the plunger 25 via the spindle thread drive 48. In doing so, the force is such that the desired pressure, e.g., 30 bar or 40 bar, will occur in the supply chamber 20. The energy supply of the battery 46 is large enough for the motor 47 to be able to eject the entire supply of the supply chamber 20 at least once. It is possible to also design this product as a single-use product or as a refillable product. The supply chamber 20 and/or the battery 36 may be designed and arranged so as to be replaceable.

The injection device 10 in accordance with the invention comprises a fluid applicator 11 that is fed by a fluid delivery arrangement 12, said fluid delivery arrangement containing an energy storage 29. Preferably, the latter is configured as the pressure vessel 36. The gas pressure derived from this pressure vessel 36 acts, either directly (FIG. 5) or indirectly (FIGS. 3, 4), on a container that has been prefilled with the fluid (e.g., isotonic NaCl solution). The fluid to be ejected is thus subject to constant pressure. With the use of a valve 23, the user can initiate the ejection of the desired amount of fluid with constant intensity. The check valve 23 may also be a regulating valve which can be used by the user to vary the intensity of the effect. The invention basically features the implementation of an always available injection device that can be produced in a highly cost-effective manner. The user need only release the system, e.g., by puncturing the pressure vessel 36, in order to then be able to directly inject the fluid in a defined or metered manner via the fluid line 18, i.e., the fluid applicator 11. Handling, releasing, as well as actuating, the check valve or regulating valve 23 is easily and intuitively possible. However, it is also possible to configure the entire injection device 10 as a single-use system and to prefill the fluid applicator 11 up to its fluid exit opening. A sterile seal at the distal end of the fluid applicator 12 can be provided by a protective cap 16.

LIST OF REFERENCE SIGNS

10 Injection device
11 Fluid applicator
12 Fluid delivery arrangement
13 Handle
14 Nozzle shaft
15 Button
16 Protective cap
17 Fluid exit opening
18 Fluid line
19 Distal end
20 Supply chamber
21 Fluid
22 Exit
23 Valve
24 Actuating member
25 Plunger
26 First movable wall surface
27 Rod
28 Drive arrangement
29 Energy storage
30 Expansion chamber
31 Second movable wall surface
32 Cylinder
33 Plunger
34 Intermediate space
35 Vent opening
36 Pressure vessel, pressure source
37 $CO_2$ cartridge
38 End
39 Seal
40 Puncturing needle
41 Channel
42 Exit opening
43 Compression spring
44 Pull rod
45 Locking arrangement
46 Battery, rechargeable battery
47 Motor
48 Spindle thread drive
49 Switch
50 Handling means

What is claimed is:
1. Injection device (10) comprising:
 a fluid applicator (11) comprising:
  a fluid exit opening (17) configured to provide needleless injection of a fluid into a biological tissue, and
  a fluid line (18) leading to the fluid exit opening (17);
 a fluid delivery arrangement (12) comprising a drive arrangement (28) configured to connect to a supply chamber (20), wherein the supply chamber (20) comprises at least one first movable wall surface (26) to which can be applied a force generated by the drive arrangement (28), wherein the drive arrangement (28) comprises:
- an energy storage (29) comprising a pressure-storing pressure vessel (36), and
- an expansion chamber (30) that has a second movable wall surface (31) to which a pressurized fluid can be applied by the energy storage (29), wherein the drive arrangement is configured to provide a substantially constant ejection pressure to the fluid during ejection of the fluid from the fluid exit opening, wherein the first movable wall surface (26) and the second movable wall surface (31) have different areas with the first movable wall surface (26) having an area larger than that of the second movable wall surface (31), wherein the first movable wall surface (26) and the second movable wall surface (31) have areas having a ratio of 1:2.

2. Injection device as in claim 1, wherein the pressure vessel (36) is a CO2 cartridge (37) provided with a gas-tight seal (39).

3. Injection device as in claim 2, wherein the energy storage (29) is associated with a change receptacle for the pressure vessel (36) and with a puncturing arrangement (40) for the seal (39).

4. Injection device as in claim 1, wherein a vented space (34) is arranged between the first wall surface (26) and the second wall surface (31).

5. Injection device as in claim 1, further comprising a valve (23) interposed between the supply chamber (20) and the fluid exit opening (17).

6. Injection device as in claim 5, wherein the valve (23) is a check valve.

7. Injection device as in claim 5, wherein the valve (23) is a regulating valve.

8. Injection device as in claim 1, wherein the fluid exit opening (17) is provided with a protective cap (16).

9. Injection device as in claim 1, wherein the pressure-storing pressure vessel (36) is configured to provide the pressurized fluid at about 55 bar to 60 bar to effect the constant ejection pressure to be about 30 bar.

* * * * *